(12) United States Patent
Bhattacharjee et al.

(10) Patent No.: US 7,018,636 B1
(45) Date of Patent: Mar. 28, 2006

(54) VACCINE AGAINST GRAM-NEGATIVE BACTERIAL INFECTIONS

(75) Inventors: Apurba Bhattacharjee, Kensington, MD (US); Alan Cross, Chevy Chase, MD (US); Jerald Sadoff, Washington, DC (US); Wendell Zollinger, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 08/886,044

(22) Filed: Jun. 30, 1997

Related U.S. Application Data

(63) Continuation of application No. 08/230,402, filed on Apr. 20, 1994, now abandoned.

(51) Int. Cl.
*A61K 39/385* (2006.01)
*A61K 39/02* (2006.01)
*A61K 39/095* (2006.01)
*A01N 43/04* (2006.01)
*C07H 1/00* (2006.01)

(52) U.S. Cl. .............. 424/197.11; 424/234.1; 424/184.1; 424/241.1; 424/250.1; 424/257.1; 424/259.1; 424/260.1; 514/23; 536/123.1; 530/350; 530/825; 530/806

(58) Field of Classification Search ............. 424/257.1, 424/251.1, 197.11, 234.1, 184.1, 250.1, 259.1, 424/260.1, 241.1; 514/2, 23; 536/123.1; 530/350, 300, 825
See application file for complete search history.

(56) References Cited

U.S. PATENT DOCUMENTS 4,707,543 A * 11/1987 Zollinger et al. ............ 530/402
4,918,163 A * 4/1990 Young ........................ 530/387

FOREIGN PATENT DOCUMENTS

| GB | A-0 109 688 | 6/1984 |
| WO | WO 87/07148 | * 12/1987 |
| WO | WO 91/01755 | * 2/1991 |

OTHER PUBLICATIONS

Teng et al. PNAS 82: 1790-1794, abstract, 1985.*
Wickstrom et al. Vet. Microbiol. 13: 259-271, abstract, 1987.*
Jachymek W. Postepy Hig Med. Dosw. 49: 171-178, abstract, 1995.*
Tomita et al. J. Dairy Sci. 76: Suppl. 1: p. 159, abstract, 1993.*
Spier et al. Circ. Shock. 28: 235-248, abstract, 1989.*
Ziegler et al. Clin Res. 29: p. 576A, abstract, 1981.*
Yoshioka et al. Res. Commun. Chem. Pathol. Pharmacol. 80: 367-370, abstract, 1993.*
Tyler et al. Am. J. Vet. Res. 55: 1256-1260, abstract, 1994.*
Tyler et al. J. Dairy Sci. 74: 1235-1242, 1991.*
Tyler et al. J. Immunol. Methods 129: 221-226. 1990.*
Tyler et al. Am. J. Vet. Res. 49: 1950-1954, 1988.*
Pollack et al. J. Clin. Invest. 72: 1874-1881, 1983.*
Ding et al. J. Med. Microbiol. 31: 95-102, 1990.*
Nixdorff et al. In: Microbial Infections. (Eds) H. Friedman et al. Plenum Press, New York, 49-61, 1992.*
Young et al. J. Clin Invest. 56: 850-861, 1975.*
Ziegler et al. In: Seminars in Infectious Disease. (Eds) Weinstein et al. vol. IV, 366-369, 1982.*
Liu et al. PNAS 89: 4633-4637, 1992.*
Marks et al. J. Clin. Invest. 69: 742-749, 1982.*
Cryz Jr. et al. Eur. J. Clin. Microbiol. 4: 180-185, 1985.*
Moreno et al. Infect. Immun. 47: 527-533, 1985.*
Cohen et al. Lancet 1: 8-10, 1987.*
Hawe et al. In: Abstracts of papers presented in the Meeting on Modern Approaches to New Vaccines, Cold Spring Harbor Labortory, Sep. 16-20, 1992.*
Lugowski et al. J. Immunol. Methods 95: 187-194, 1986.*
Tyler et al. J. Dairy Sci. 75: 1821-1825, 1992.*
Tomita GM. Immunization of dairy cows against coliform mastitis. Dissertation, The Ohio State University, 1985.*
Tyler et al. J. Vet. Intern. Med. 4: 17-25, 1990.*
McCullus et al. Infect. Immun. 55: 1042-1046, abstract, 1985.*
Bhattacharjee et al. Infect. Dis. Clin. North Amer. 13: 355-369, Jun. 1999.*
Schwartzer et al. J. Infect. Dis. 158: 1135-1136, 1985.*
Cross et al, Infection & Immunity 61:2741-2747, 1993.*
Colandru et al The Journal of Infectious Dis. 158: 312-319, 1988.*
Mandrell et al, Infection & Immunity 57: 1590-1598 1989.*
Moreno et al, Infection & Immunity 47:527-533 1985.*
Cross et al Journal of Endotoxin Research 1994, pp. 57-69.*
Greenman et al JAMA 266:1097-1102, 1991.*

(Continued)

*Primary Examiner*—S. Devi
(74) *Attorney, Agent, or Firm*—Elizabeth Arwine; Charles H. Harris; John Francis Moran

(57) ABSTRACT

A vaccine, effective in inducing the production of antibodies with which to immunize a second subject passively against infection by Gram-negative bacteria and LPS-mediated pathology, comprises a non-covalent polyvalent complex formed between purified, detoxified LPS derived from *E. coli* and purified outer membrane protein derived from *N. meningitidis*. The same vaccine will also actively immunize a host subject against Gram-negative bacterial infections and LPS-mediated pathology. Meningococcal infections are included among those Gram-negative bacterial infections protected against by the vaccine.

8 Claims, 1 Drawing Sheet

OTHER PUBLICATIONS

Moore te al. Translplantation 44: 249-253, 1987.*
Dunn et al. Surgery 96: 440-446, 1984.*
Braude et al J. Infect. Dis. 136: Suppl. S167-S173, 1997.*
Ziegler et al. J. Immunol. 111: 433-438, 1973.*
Campnagari et al. Microb. Pethogen. 8: 353-362, abstract, 1990.*
Zollinger et al. J. Clin. Invest. 63: 836-848, 1979.*
Salles et al. J. Infect. Dis. 159: 641-647, 1989.*
Fenwick et al. Am. J. Vet. Res. 47: 1888-1891, abstract, 1986.*
Fenwick et al. Infect. Immun. 53: 298-304, abstract, 1986.*
Nelles et al. Infect. Immun. 46: 677-681, 1984.*
Kanegasaki et al. In: Bacterial Endotoxin: Chemical, biological and clinical aspects. (Ed) Homma et al. Verlag Chemie, pp. 149-158, 1984.*
Tomita Dissertation Abstracts International, vol. 56, abstract, 1994.*
Said et al. J. Biol. Chem. 256: 7305-7310, abstract, 1981.*
Gu et al. J. Clin. Microbiol. 30: 2047-2053, 1992.*
Tomita et al. J. Dairy Sci. 78: 2178-2185, 1995.*
Tomita et al. J. Dairy Sci. 78: 2745-2752, 1995.*
Dale et al. J. Infect. Dis. 166: 316-325, 1992.*
McCabe et al. Prog. Clin. Biol. Res. 47: 107-117, 1980.*
Braude et al. J. Infect. Dis. 136: S167-A173, 1977.*
Cryz et al. Eur. J. Clin. Microbiol. 4: 180-185, abstract, 1985.*
Lugawski C. Acta Biochim. Pol. 42: 19-24, 1995.*
Davis et al. J. Exp. Med. 147: 1007-1017, abstract, 1978.*
Alan S. Cross. Annals of Int. Med. 121: 58-60, Jul. 1, 1994.*

* cited by examiner

Neutropenic Rat Survival Curves

— + — R#62 Post IgG
--- △ --- R#42374 IgG
--- ○ --- Preimmune IgG
······ + ······ PBS Control

VACCINE AGAINST GRAM-NEGATIVE BACTERIAL INFECTIONS

This application is a continuation of application Ser. No. 08/230,402, filed Apr. 20, 1994, now abandoned.

BACKGROUND OF THE INVENTION

1. Field of the Invention

This invention relates to a vaccine effective against infections with Gram-negative bacteria and lipopolysaccharide ("LPS")—mediated pathology induced by Gram-negative bacterial infections. More particularly, it relates to a non-covalent, polyvalent complex vaccine containing purified *E. coli* LPS endotoxin and purified *N. meningitidis* outer membrane protein, which vaccine produces, in an actively immunized subject, an immune response against Gram-negative bacterial infection and the pathology caused by the LPS endotoxin. The present invention also relates to production of specific polyclonal antibodies that can be used to protect a second subject passively against Gram-negative bacterial infections and LPS-mediated pathology.

2. Description of the Background Art

Infections by Gram-negative bacteria and consequent septic shock are leading causes of death among hospitalized patients. It is estimated that Gram-negative sepsis has an incidence of 70,000 to 300,000 cases per year in the United States. McCabe et al., *Am. J. of Med.* 68: 344 (1980).

It is well-documented that a principal mediator of Gram-negative bacterial septic shock is a LPS endotoxin present on the outer membrane of Gram-negative bacteria. Luderitz et al., *Rev. Infect. Dis.* 61: 428 (1984); Rietsckel et al., *loc. cit.* 9 (suppl.): 5527 (1987).

Attempts have been made to produce vaccines that will produce anti-endotoxin antibodies, and thereby protect against septic shock. For a review, see Cross et al., *J. Endotox. Res.* 3: 57 (1994). Ziegler et. al., *N. Eng. J. Med.* 107: 1225 (1982) showed in a clinical setting that polyclonal antiserum obtained from volunteers immunized with boiled *E. coli* J5 (Rc chemotype) provided significant protection. In another study, however, the human polyclonal antibody to J5 boiled cell vaccine was not superior to normal human IgG in reducing death from Gram-negative bacteremia. Calandra et al., *J. Infect. Dis.*, 158:312 (1988). On the other hand, more recently it was shown that affinity-purified IgG derived from the serum of rabbits immunized with J5 boiled cell vaccine afforded neutropenic rats substantial protection against challenge with *Ps. aeruginosa*, a heterologous Gram-negative bacteria. Bhattacharjee et al., *Clin. Res.* 41 (2): Abs 247 (1993). These contradictory reports point up the uncertainty and unpredictability of using boiled J5 LPS as a vaccine.

Disappointing results also have been reported in the use of anti-endotoxin monoclonal antibodies. Clinical trials of the HA-1A human monoclonal antibody (Ziegler et al., *N. Eng. J. Med.* 324: 429 (1991)), and the E5 murine monoclonal IgM antibody (Greenman et al., *J. Am. Med. Assoc.* 266: 1097 (1991); Wenzel et al., 31 st Intl. Conf. Antimicrob. Agts. Chemotherapy 240, Abstr. 1170 (1991)) did not generate data adequate to support product licensing. Cross et al. (1994), above.

Earlier, Kanegasaki et al. in BACTERIAL ENDOTOXIN: CHEMICAL, BIOLOGICAL AND CLINICAL ASPECTS, Homma et al., eds. (Verlag Chemie, 1984), complexed various crude LPS preparations with an outer membrane protein derived from *E. coli* and compared these complexes in two systems, namely, induction of interferon production in rabbit spleen cells and activation of preclotting enzymes of the horseshoe crab. It was reported that differing degrees of activity were exhibited by complexes derived from different LPS preparations, and that substituents not masked after complex formation are in part responsible for the variability of activity. This, in turn, may be a reflection of the great variability of the O-polysaccharide chain structure of LPS's even among different strains of the same species. For example, there are over 100 serotypes of *E. coli* based on the structure of O-polysaccharide. Kenne et al. in 2 POLYSACCHARIDES 282, G. O. Asoinall, eds. (1983).

Because of these uncertainties and an unmet need of long-standing for a vaccine effective against Gram-negative bacterial infections, the present inventors have devised a novel vaccine which allows for both active and passive immunization against Gram-negative bacterial infections.

SUMMARY OF THE INVENTION

It is therefore an object of the present invention to provide a means of both actively and passively immunizing a subject against Gram-negative bacterial infections and LPS pathology. In this regard, a subject can be actively immunized with a non-covalent vaccine comprising a complex between purified *E. coli* LPS and purified outer membrane protein ("OMP") derived from *N. meningitidis*. Serum or plasma from an actively immunized subject, or IgG isolated therefrom (hereafter "specific polyclonal antibody"), can be administered to a second subject to confer on the latter a passive protection against Gram-negative bacterial infections and LPS-mediated pathology, including sepsis.

It is another object of the present invention to provide a purified, detoxified LPS endotoxin from an *E. coli* strain suitable for use in the aforementioned non-covalent complex vaccine.

It is still another object of this invention to provide a purified outer membrane protein from an *N. meningitidis* strain suitable for use in the aforementioned non-covalent complex vaccine.

It is yet another object of the invention to provide a non-covalent complex between purified, detoxified LPS endotoxin from *E. coli* and purified outer membrane protein from *N. meningitidis*.

Another object of the present invention is to provide a method of passively immunizing a subject against Gram-negative bacterial infections using plasma or post-immune serum (antiserum), or specific polyclonal antibody purified therefrom, obtained from a host subject actively immunized with the aforementioned non-covalent complex vaccine.

Yet another object of the invention to provide a method of using the non-covalent complex vaccine of the invention for active or passive immunization of a subject against meningococcal infections.

These and other objects will become apparent by reference to the specification and examples below.

DETAILED DESCRIPTION OF THE PREFERRED EMBODIMENTS

Figure 1:
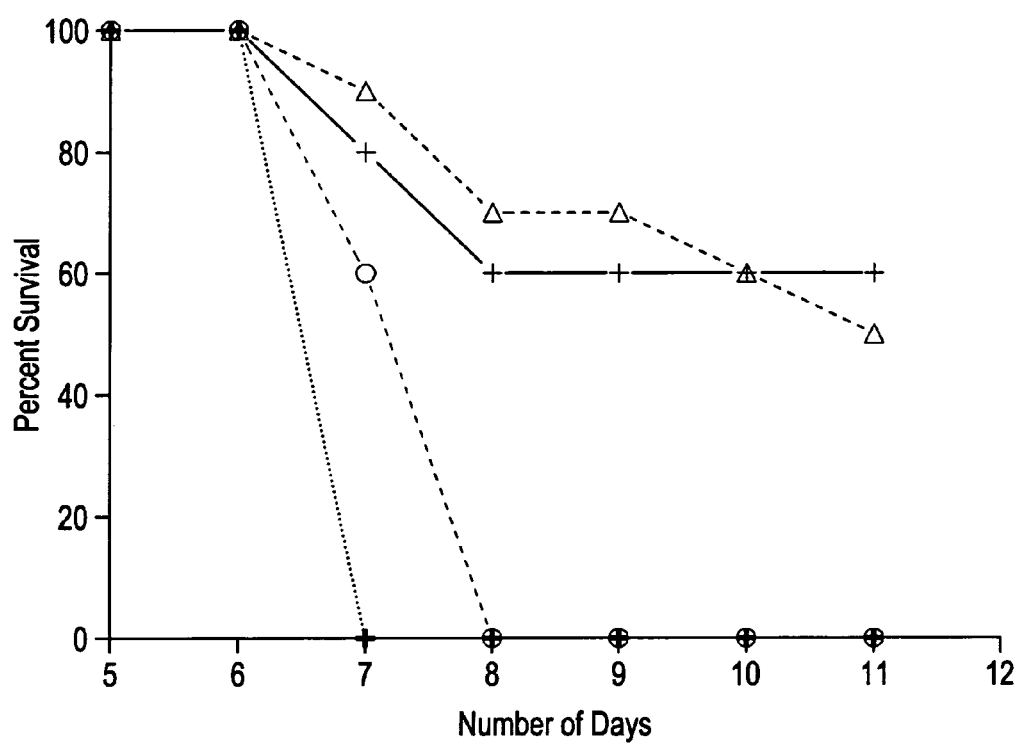
FIG. 1 shows survival data from the neutropenic rat model of sepsis, wherein the rat is treated with IgG isolated from the post-immune serum of a rabbit immunized with J5 LPS-GBOMP non-covalent complex vaccine (R #62, post-immune serum IgG, +---+); IgG isolated from the serum of rabbit # 42374 that was immunized against J5 DLPS-GBOMP (Δ--Δ); Preimmune rabbit serum IgG (-o-); PBS control (+---+).

According to the present invention, a non-covalent, polyvalent complex between purified, detoxified LPS ("DLPS") derived from E. coli and purified outer membrane protein derived from N. meningitidis is provided which, when injected into a host subject, actively immunizes the host subject against Gram-negative bacteria and LPS-mediated pathology. Post-immune serum or plasma from the host subject, or specific polyclonal antibody purified from these fluids, can be administered to a second subject, passively immunizing the second subject against infection by Gram-negative bacteria and LPS-induced pathology.

The preferred strain of E. coli from which to prepare purified and detoxified LPS endotoxin is an E. coli J5 (Rc chemotype) strain. Native J5 LPS may be purchased from List Biological Labs, Inc., Campbell, Calif. For purification purposes it is preferred that the LPS preparation contain less than about 1% protein and less than about 1% nucleic acid. By "purified E. coli LPS" is meant LPS suitable for use in the invention vaccine prepared by sonicating native LPS in an alkaline solution, heating the solution at 65° C., neutralizing the cooled solution to pH 7.0, removing released fatty acids and remaining native LPS by Sephadex G-50 chromatography, and collecting the purified, detoxified DLPS. As determined in a standard rabbit pyrogenicity test, this method reduces the pyrogenicity of LPS preparations, and thus are also referred to as DLPS. An embodiment of this procedure is described in Example 1 below.

A preferred strain of meningococcus is N. meningitidis group B. The outer membrane protein therefrom (hereinafter "GBOMP") is prepared as described in Zollinger et al., J. Clin. Invest. 63:836 (1079), and U.S. Pat. No. 4,707,543 (1987), the contents of which are incorporated herein by reference. Briefly, meningococcal group B cells are warmed to about 55 to 60° C. for a brief period, and disrupted in a shearing device such as OMNIMIX, sold by DuPont Instruments (Newtown, Conn.). The shearate is centrifuged at forces up to 100,000×g to isolate in the pellet the outer membrane complex ("OMC"). The OMC is dissolved in buffered detergent, and repeatedly fractionated with ammonium sulfate so as to collect purified GBOMP precipitating at 0.5 g/ml salt. The protein is then ultrafiltered through a membrane. This preparation will be referred to herein as "purified outer membrane protein". Details of one embodiment are provided in Example 2 below.

To prepare the inventive non-covalent complex, solutions of GBOMP and J5 LPS are mixed, incubated at room temperature until complex formation has occurred (0.5 to 2 hrs.), and dialyzed repeatedly against sterile isotonic saline for 3 to 5 days in the cold. Any insoluble material is removed by centrifugation and by filtering through a membrane (e.g., 0.45 µm, Amicon). The vaccine complex is preferably stored in the cold (5° C.) until use. The protein concentration of the vaccine is generally adjusted to about 1 to 3 mg/ml. In general, the ratio of GBOMP to J5 LPS in such complexes is about 1–2. Embodiments of this procedure are provided in Examples 3 and 4.

The immunogenicity of the J5 LPS-GBOMP non-covalent complex vaccine may be tested in a rabbit system. Rabbits (preferably New Zealand white rabbits, Hazelton Res. Prods., Denver Pa.) are injected intramuscularly with a sterile saline solution of the above-described complex vaccine. It is preferred that each rabbit receive a total of 3 doses of the vaccine. Control animals may be used to test variables, such as individual components of the vaccine complex and vaccine dosage. Post-immune serum is collected from the immunized rabbits, and the amount of anti-LPS antibody present in their serum determined by an ELISA test. IgG can be isolated from this post-immune serum or plasma conventionally. Two embodiments of this procedure are shown in Example 7 and Example 8, respectively.

The aforementioned ELISA test is performed in microtitre plates essentially by the method of Engvall et al., J. Immunol. 109: 129 (1972), with slight modifications as will be described in detail in Example 6 below. Briefly, wells are coated with poly-L-lysine (Sigma Chem. Co., St. Louis, Mo.), and coats overlaid with either J5 LPS or lipid A. Antigen (Ag)-coated plates, after blocking nonspecific binding sites with a foreign protein, for example, casein, are incubated with serial dilutions of the rabbit serum containing antibodies (Ab) A second, enzyme-tagged antibody (Ab-E) is added to form an $Ag-Ab_1-Ab_2-E$ complex, and the presence and amount of Ag determined calorimetrically with a chromogen (p-nitrophenyl phosphate). Absorbancies may be determined automatically, for example, using the DYNATECH PLATE READER produced by Dynatech (Alexandria, Va.). ELISA absorbancy units are calculated by multiplying the serum dilution by the $A_{410nm}$ at an absorbancy reading near the midpoint of the linear portion of the standard curve. These procedures are described in Example 6 below.

A vaccine within the present invention will be useful for active immunization of populations at risk of acquiring septic shock, such as surgery patients, the military, police and firemen. In addition, human volunteers can be safely actively immunized with this non-covalent complex, and antibodies prepared from such human hyperimmune sera can be used for passive protection of patients, including domestic and other animals, against Gram-negative bacterial infections and sepsis.

The above-described non-covalent complex is simple to prepare and is highly cost effective. Unlike the original boiled J5 LPS vaccine employed by Ziegler et al. (1982) above, the present complex is prepared from purified, detoxified J5 LPS and purified GBOMP, and is thus well defined and preferable over the prior art boiled whole bacterial cell vaccines. The J5 LPS can be prepared in large quantities suitable for clinical use.

This is the first successful use of a purified, detoxified J5 LPS in a vaccine formulation.

The following examples are intended to illustrate preferred embodiments of this invention, and are not intended to limit the scope of the invention which is defined by the specification and appended claims.

EXAMPLE 1

Preparation of Purified, Detoxified J5 LPS (J5 DLPS)

The lipopolysaccharide (LPS) from E. coli J5 (Rc chemotype, J5 LPS, lot #16A) was purchased from List Biological Laboratories Inc. (Campbell, Calif.). This preparation contained less than 1% protein and less than 1% nucleic acid as determined by absorbances at 260/280 nm.

In view of the fact that the native J5 LPS was pyrogenic in the rabbit pyrogenicity test at a dose of 0.01 µg, it was necessary to prepare a detoxified J5 LPS for use in making a J5 DLPS-GBOMP non-covalent complex vaccine.

Native E. coli J5 LPS (10 mg) was dissolved into 4.5 ml of 0.1 M NaOH solution, and then sonicated for 5 minutes. The slightly hazy solution was heated in a screw-capped tube at 65° C. for 2 hours. The cooled solution was neutralized with 1.0 M HCl to a pH of about 7.0. The released fatty acids and any remaining native J5 LPS were removed by chromatography on Sephadex G-50 (1.6×60 cm) using 0.01 M pyridine-acetate buffer pH 6.5 as eluant. The purified, detoxified J5 LPS (J5 DLPS) eluted shortly after the void volume. The fractions were combined and lyophilized (yield=6.5 mg). Such preparations were pyrogen-free at the 0.5 µg level of DLPS (see Example 5).

EXAMPLE 2

Purification of N. Meningitidis Group B Outer Membrane Protein

Neisseria meningitidis GBOMP was prepared by methods described previously. See Zollinger et al., *J. Clin. Invest.* 63: 836–48 (1979), and U.S. Pat. No. 4,707,543, the respective contents of which are incorporated herein by reference. Briefly, meningococcal group B cells from strain #8529 (collection of Walter Reed Army Institute of Research, Washington, D.C.) from a 15 liter culture, collected by continuous centrifugation (135 g, wet wt.), were suspended in 300 ml buffer containing 0.05 M Tris-chloride, 0.15 M NaCl and 0.01 M EDTA, pH 7.4 and warmed at 56° C. for 30 minutes. The suspension, cooled to room temperature, was sheared in an Omnimixer (DuPont Instruments, Newton, Conn.) at full speed for 3 minutes and centrifuged at 30,000×g for 20 minutes. The pellets were re-extracted in the same way and the supernates were combined. The combined supernate was centrifuged at 25,000×g for 15 minutes. The resulting supernate was centrifuged at 100, 000×g for 1 hour, and the pelleted outer membrane complex (OMC) was suspended in about 150 ml of distilled water by magnetic stirring. The suspension was centrifuged at 10,000×g for 15 minutes and the resulting supernate was centrifuged at 100,000×g for 1 hour. The pelleted OMC was suspended in about 75 ml of distilled water and to this suspension was added 75 ml of 2× TEEN buffer (2% Empigen BB, 0.35 M NaCl, 0.021 M EDTA, 0.10 M Tris-HCl, pH 8.0). The mixture was magnetically stirred for 1 h.

Solid ammonium sulfate (500 g/L) was added to the OMC suspension, and the mixture was stirred until all the ammonium sulfate was dissolved. The suspension was allowed to stand at room temperature for 1 hour and then centrifuged at 20,000×g for 20 minutes. The precipitated protein collected at the top of the tube was recovered by drawing off liquid from the bottom. The protein was redissolved in 150 ml of TEEN buffer (1% Empigen BB, 0.15 M NaCl, 0.01 M EDTA and 0.05 M Tris-HCL, pH 8.0). The precipitation was repeated two more times using 600 g/L of ammonium sulfate. The final precipitate was dissolved in TEEN buffer at 1–2 mg/ml and dialyzed against 4 changes of 20 volumes of TEEN buffer (containing 0.1% Empigen BB) to remove the ammonium sulfate. This outer membrane preparation was combined with more OMP extracted from the pelleted cells using detergent as follows.

The pelleted cells were suspended in about an equal volume of 1 M sodium acetate buffer pH 4.9 and 3 volumes of distilled water were added. To this mixture was added 5 volumes of a solution containing 6% Empigen BB in 1.0 M calcium chloride. The mixture was stirred at room temperature for 1 h., after which ethanol was added to a concentration of 20% volume/volume. The resulting precipitate was removed by centrifugation at about 20,000×g for 10 minutes. The pellets were discarded and the supernatant was brought to 45% ethanol volume/volume. The precipitated proteins were collected by centrifugation at about 20,000×g for 10 minutes and dissolved in TEEN buffer. Any insoluble material was removed by centrifugation at about 20,000×g for 10 minutes. The protein was further purified to remove lipopolysaccharides, capsular polysaccharide and nucleic acid by ammonium sulfate precipitation three times as described above.

The GBOMP prepared by the two sequential methods were combined and concentrated by ultrafiltration on a PM-10 membrane. The final protein concentration was 3.67 mg/ml.

EXAMPLE 3

Preparation of J5 DLPS-NMGBOMP Non-Covalent Complex

N. meningitidis group B OMP (NMGBOMP) solution 1.5 ml (3.67 mg/ml, Example 2) was added to 5.0 ml of a solution (0.8 mg/ml) of J5 (DLPS in 0.9% NaCl. The mixture was kept for 1 hour a room temperature and was then dialyzed against 100 volumes of sterile 0.9% NaCl at 5° C. for 48 hours. The dialysis buffer was changed and dialysis continued at 5° C. for another 72 hours. The dialyzed solution (5.5 ml) was slightly hazy. This solution was filtered through 0.45 µm membrane and stored at 5° C. Analysis showed that this J5 DLPS-NMGBOMP non-covalent complex vaccine had J5 DLPS=600 µg/ml and NMGBOMP=1.0 mg/ml.

EXAMPLE 4

Preparation of J5 LPS-N. Menigitidis GBOMP Non-covalent Complex

In another preparation, 5 mg of J5 LPS was dissolved in 5 ml of sterile 0.9% NaCl for injection, USP (Kendall and McGaw, lot #JOBO29A). This gave a hazy suspension. The suspension was sonicated for 10 minutes in an Ultrasonic bath (Branson, model 5200). It remained a hazy suspension. 1.4 ml of GBOMP solution (3.67 mg/ml from Example 2) was added to the J5 LPS suspension. The mixture became clear immediately. This clear solution was dialyzed in 150 volumes of sterile 0.9% NaCl (injection quality, USP) at 5° C. for 5 days. The dialyzed solution was slightly hazy. The insoluble material was removed by centrifugation at 10,000×g for 20 minutes. The clear supernate (vaccine #1) was stored at 5° C. until used. The ratio of GBMOMP:J5 LPS was found to be 1.5:1 (w/w). A portion (3.0 ml) of this preparation was filtered through a 0.45 µm membrane. The filtered sample (vaccine #2) was stored at 5° C. until used. This second vaccine addresses the possible effect of a filtration step in the preparation of a sterile vaccine. The ratios are slightly altered. The mass ratio of GBOMP to J5 LPS in representative complexes was 1.2:1.

EXAMPLE 5

Test for Pyrogenicity of the J5 DLPS-NMGBOMP Complex

The J5 DLPS-NMGBOMP non-covalent complex vaccine formulation was tested for pyrogenicity by the standard rabbit pyrogenicity assay. This vaccine was not pyrogenic at a dose containing 0.5 µg J5 DLPS. At a 10-fold higher dose (5.0 µg J5 DLPS) it was pyrogenic with an average rise in temperature of 1.3° C. (see Table 1). Based on these results, a dose containing 1.0 µg of J5 DLPS is selected. Converting this to a human dose for a 70 kg volunteer, a dose of about 35 µg of J5 DLPS is selected to provide high immunogenicity in humans.

and 33 µg J5 LPS in the complex. Rabbits #64 and 65 received the vaccine that was filtered through a 0.45µ membrane (vaccine #2); 50 µg GBOMP and 41 µg J5 LPS were present in each dose. The rabbits received a total of three doses of vaccine. As shown in Table 2, the rabbits

TABLE 1

| Lot # | SAMPLE | DOSE µg | RABBIT # | MAXIMAL RISE ° C. | AVERAGE | Pyrogenicity |
|---|---|---|---|---|---|---|
| AKBXV80.1 | J5 LPS-OMP | 0.06 | 2789 | 1.2 | | |
| AKBXV80.1 | J5LPS-OMP | 0.06 | 2790 | 1.6 | | |
| AKBXV80.1 | J5LPS-OMP | 0.06 | 2791 | 1.2 | 1.3 | |
| AKBXV80.2 | J5 dLPS-OMP | 0.05 | 2780 | 0.1 | | |
| AKBXV80.2 | J5 dLPS-OMP | 0.05 | 2781 | 0.4 | | |
| AKBXV80.2 | J5 dLPS-OMP | 0.05 | 2782 | 0.1 | 0.2 | PASS |
| AKBXV80.2C | J5 dLPS-OMP | 0.5 | 2783 | 0.5 | | |
| AKBXV80.2C | J5 dLPS-OMP | 0.5 | 2784 | 0.0 | | |
| AKBXV80.2C | J5 dLPS-OMP | 0.5 | 2785 | 0.1 | 0.2 | PASS |
| AKBXV80.2D | J5 dLPS-OMP | 5.0 | 2788 | 1.6 | | |
| AKBXV80.2D | J5 dLPS-OMP | 5.0 | 2801 | 1.3 | | |
| AKBXV80.2D | J5 dLPS-OMP | 5.0 | 2802 | 1.4 | 1.4 | |
| AKBXV80.4B | J5 dLPS | 0.05 | 2792 | 1.1 | | |
| AKBXV80.4B | J5 dLPS | 0.05 | 2793 | 1.1 | | |
| AKBXV80.4B | J5 dLPS | 0.05 | 2794 | 1.7 | 1.3 | |
| AKBXV80.4C | J5 dLPS | 0.5 | 2779 | 2.1 | | |
| AKBXV80.4C | J5 dLPS | 0.5 | 2786 | 2.3 | | |
| AKBXV80.4C | J5 dLPS | 0.5 | 2787 | 2.0 | 2.1 | |

EXAMPLE 6

Enzyme-linked Immunosorbent Assay (ELISA)

The ELISA was performed in 96 well flat-bottom polystyrene microtiter plates (Costar, Cambridge, Mass.) essentially by the method of Engvall et al. above) with slight modification. The wells were first coated with 50 µg/ml poly-L-lysine type VIIB in PBS (0.01 M Na-phosphate, 0.14 M NaCl, 0.02% NaN$_3$ pH 7.4) 100 µl, at 37° C. for 1 hour. The wells were emptied and then overlaid with either J5 LPS or lipid A at 10 µg/ml in PBS for 3 hours at 37° C. Excess binding sites were then blocked with 1% casein (Fisher Scientific Co., Columbia, Md.) in PBS at 37° C. for 1 hour. The wells were washed with PBS between steps to remove unbound material. The antigen-coated plates were incubated with serial 2-fold dilutions of antibodies for 16 hours at room temperature (25° C.). Incubation with the second antibody was performed for 20 hours at room temperature. Disodium p-nitrophenylphosphate (Sigma Chemical Co.) at a concentration of 1 mg/ml in (1.0 M diethanolamine buffer, with 1 mM MgCl$_2$), pH 9.8 was used as the substrate. Absorbance was read on a Dynatech plate reader (Dynatech; Alexandria, Va.) at 410 nm. The ELISA O.D. units were calculated by multiplying the dilution of the serum with the absorbance at 410 nm at an O.D. reading near 0.5. The O.D. reading of 0.5 is at about the midpoint of the linear part of the O.D. vs dilution curve in our assay.

EXAMPLE 7

Immunogenicity of J5 LPS-N. Meningitidis Non-covalent Complex Vaccine in Rabbits Two groups of 2 each New Zealand white rabbits (Hazelton Research Products, Denver, Pa.), were immunized with the two vaccines in saline by intramuscular injection. The immunogenicity data are shown in Table 2. Each rabbit received a dose containing 50 µg of GBOMP. Rabbits #62 and 63 each received vaccine #1 which has 50 µg GBOMP showed about a 40 to 142-fold rise in ELISA titer against J5 LPS four weeks after the first injection and another 4 to 6-fold rise one week after the second injection. The ELISA titers dropped somewhat after the second injection, but rose after the third injection. The ELISA titers against lipid A were much lower, and showed only a marginal rise of 1.2 to 2.5-fold over pre-immunization levels.

TABLE 2

Immunogenicity of J5 LPS-N. meningitidis GBOMP Non-covalent Complex Vaccine in Rabbits ELISA Titers of Pre- and Postbleed Sera From Rabbit # 62–65*

| Rabbit# | Prebleed | 2/18/92 | 2/25/92 | 3/18/92 | 4/07/92 | FOLD |
|---|---|---|---|---|---|---|
| Elisa Titer in O.D. Units vs J5 LPS | | | | | | |
| 62 | 106 | 3,955 | 25,804 | 7,014 | 20,019 | 188 |
| 63 | 99 | 4,115 | 14,873 | 7,411 | 8,332 | 84 |
| 64 | 32 | 3,558 | NA | 3,142 | 6,054 | 189 |
| 65 | 32 | 4,550 | 16,384 | 3,891 | 13,900 | 434 |
| ELISA Titers vs E. coli Lipid A | | | | | | |
| 62 | 93 | 147 | 276 | 163 | 236 | 2.5 |
| 63 | 185 | 281 | 323 | 281 | 261 | 1.4 |
| 64 | 68 | 97 | NA | 83 | 124 | 1.8 |
| 65 | 270 | 341 | 364 | 334 | 345 | 1.2 |

The first injection was given on 1/16/92; the second injection was given on 2/18/92 and the third injection was given on 3/18/92.
*Rabbit #62–63 received the vaccine #1 and rabbit #64–65 received the vaccine #2.
NA Not available because serum was lost due to breakage of tube.

EXAMPLE 8

Immunogenicity of J5 DLPS-NMGBOMP Vaccine in Rabbits

Five groups of New Zealand white rabbits (2 rabbits in each group) were immunized with the J5 DLPS-NMG-BOMP non-covalent complex vaccine. Group #1 received the complex containing 25 µg J5 DLPS. Group #2 received the same dose+QS21 (a saponin adjuvant). Group #3 received the complex containing 2 μg J5 DLPS. Group #4 received the same dose as group #3+QS21. Group #5 was a control group receiving 25 μg J5 DLPS (without NMG-BOMP)+QS21. All rabbits were given 3 doses of vaccine at intervals of two weeks. The immunogenicity data are shown in Table 3. The post-immune sera from rabbits in groups 1–4 showed a 30 to 1600-fold rise in titer against the J5 LPS. There was no significant difference between group #1 and 2. The ELISA antibody titers against NMGBOMP showed 100 to 300-fold rise in titer. Again there was no significant difference between groups #1 and 2, indicating that the QS21 did not enhance the immune response to the DLPS component of this vaccine.

TABLE 3

ELISA Titers of Pre- and Post-Bleed Sera from Rabbits Immunized with J5 DLPS-GBOMP Non-covalent Complex Vaccine

| Group | Rabbit # | Prebleed | Post-1 | Post-2 | Post-3 |
|---|---|---|---|---|---|
| ELISA Titers in O.D. Units vs J5 LPS | | | | | |
| 1 | 44660 | 96 | 1,980 | 3,987 | 3,430 |
|   | 42374 | 52 | 2,035 | 5,299 | 8,243 |
| 2 | 44760 | 151 | 1,139 | 3,219 | 3,961 |
|   | 44877 | 206 | 1,856 | 2,816 | 2,688 |
| 3 | 46170 | 32 | 226 | 1,891 | 1,392 |
|   | 46880 | 40 | 432 | 3,513 | 4,614 |
| 4 | 40004 | 33 | 345 | 7,052 | 3,622 |
|   | 46298 | 305 | 635 | 3,276 | 4,012 |
| 5 | 46277 | 104 | 90 | 106 | 124 |
|   | 46886 | 24 | 31 | 37 | 51 |
| ELISA Titers in O.D. Units vs PA 134VA LPS | | | | | |
| 1 | 44660 | 59 | 296 | 150 | 144 |
|   | 42374 | 1,092 | 1,067 | 1,238 | 3,347 |
| 2 | 44760 | 1,187 | 2,297 | 1,388 | 1,907 |
|   | 44877 | 75 | 78 | 88 | 78 |
| 3 | 46170 | 10 | 16 | 22 | 22 |
|   | 46880 | 183 | 652 | 753 | 753 |
| 4 | 40004 | 148 | 209 | 198 | 154 |
|   | 46298 | 30 | 43 | 52 | 98 |
| 5 | 46277 | 13 | 23 | 38 | 34 |
|   | 46886 | 93 | 312 | 432 | 355 |
| ELISA Titers in O.D. Units vs. *N. meningitidis* GBOMP | | | | | |
| 1 | 44660 | 141 | 851 | 13,337 | 12,070 |
|   | 42374 | 79 | 580 | 14,684 | 26,137 |
| 2 | 44760 | 434 | 3,072 | 20,940 | 25,472 |
|   | 44877 | 109 | 1,148 | 17,792 | 17,958 |
| 3 | 46170 | 182 | 185 | 1,811 | 2,588 |
|   | 46880 | 119 | 296 | 3,859 | 4,294 |
| 4 | 40004 | 116 | 325 | 9,497 | 13,145 |
|   | 46298 | 225 | 398 | 5,516 | 7,577 |
| 5 | 46277 | 72 | 81 | 109 | 119 |
|   | 46886 | 84 | 316 | 371 | 377 |

GR #1 Received J5 DLPS-GBOMP Vaccine 25 μg
GR #2 Received J5 DLPS-GBOMP + QS21 Vaccine 25 μg
GR #3 Received J5 DLPS-GBOMP Vaccine 2.0 μg
GR #4 Received J5 DLPS-GBOMP + QS21 Vaccine 2.0 μg
GR #5 Received J5 DLPS + QS21 Vaccine 25 μg
VACCINE:QS21 RATIO = 1:2
Post-1 = 2 weeks post primary immunization
Post-2 = 2 weeks post secondary immunization
Post-3 = 2 weeks post tertiary immunization

EXAMPLE 9

Bactericidal Antibody Response

The post-immune sera from the rabbits of Example 8 was bacteriocidal against both homologous (#8529) and heterologous strains (#44/76, #8566 and #8047) of Group B meningococcus. As shown in Table 4, this vaccine elicited significant increases (4 to 32-fold) in bactericidal titer against both homologous and heterologous strains. Therefore, protection by this vaccine against group B meningococcal infection will be furthered by the antibodies to group B meningococcal outer membrane protein induced by the vaccine.

TABLE 4

Bactericidal Titers of Rabbit Sera

| Group | Rabbit # | Prebleed | Post-1 | Post-2 | Post-3 | Fold |
|---|---|---|---|---|---|---|
| Bactericidal Titers vs *N. menigitidis* Gr. B #8529 | | | | | | |
| 1 | 44660 | 4 | 8 | 32 | 32 | 8 |
|   | 42374 | 8 | 8 | 32 | 16 | 4 |
| 2 | 44760 | 8 | 16 | 128 | 128 | 16 |
|   | 44877 | 16 | 16 | 64 | 64 | 4 |
| 3 | 46170 | 16 | 16 | 16 | 16 | — |
|   | 46880 | 16 | 16 | 16 | 16 | — |
| 4 | 40004 | 16 | 16 | 32 | 64 | 4 |
|   | 46298 | 8 | 16 | 16 | 64 | 8 |
| Bactericidal Titers vs *N. menigitidis* Gr. B #8047 | | | | | | |
| 1 | 44660 | 8 | 8 | 8 | 8 | — |
|   | 42374 | 4 | 8 | 8 | 8 | 2 |
| 2 | 44760 | 4 | 8 | 8 | 16 | 4 |
|   | 44877 | 16 | 16 | 16 | 16 | — |
| 3 | 46170 | 16 | 16 | 16 | 16 | — |
|   | 46880 | 8 | 8 | 8 | 8 | — |
| 4 | 40004 | 4 | 16 | 16 | 16 | 4 |
|   | 46298 | 16 | 16 | 16 | 16 | — |
| Bactericidal Titers vs *N. menigitidis* Gr. B #8566 | | | | | | |
| 1 | 44660 | 32 | 32 | 64 | 64 | 2 |
|   | 42374 | 32 | 32 | 64 | 32 | 2 |
| 2 | 44760 | 16 | 32 | 128 | 128 | 8 |
|   | 44877 | 32 | 32 | 128 | 64 | 4 |
| 3 | 46170 | 64 | 64 | 64 | 64 | — |
|   | 46880 | 32 | 32 | 32 | 32 | — |
| 4 | 40004 | 32 | 32 | 64 | 64 | 2 |
|   | 46298 | 32 | 64 | 64 | 128 | 4 |
| Bactericidal Titers vs. *N. menigitidis* Gr. B #44/76 | | | | | | |
| 1 | 44660 | 4 | 4 | 32 | 32 | 8 |
|   | 42374 | 8 | 8 | 32 | 8 | 4 |
| 2 | 44760 | 4 | 16 | 128 | 128 | 32 |
|   | 44877 | 8 | 8 | 64 | 64 | 8 |
| 3 | 46170 | 8 | 16 | 16 | 16 | 2 |
|   | 46880 | 4 | 4 | 16 | 8 | 4 |
| 4 | 40004 | 8 | 8 | 32 | 64 | 8 |
|   | 46298 | 8 | 32 | 32 | 64 | 8 |

Strain #8529 = B:15:P1.3:L3, 7, 9
Strain #8047 = B:2b:P1.2:L2, 4
Strain #8566 = B:4:P1.15:L3, 7, 9
Strain #44/76 = B:15:P1.16:L3, 7, 9

EXAMPLE 10

Cross-reactivity of IgG from Post-Immune Serum of Rabbit #42374

IgG was isolated from the post-immune serum of rabbit #42374 (J5 DLPS-NMGBOMP vaccine) by affinity chromatography on Protein G-Sepharose. IgG was also isolated from pre-immune rabbit serum as a control. Bacteria grown, washed, and incubated with normal or J5 vaccine IgG, followed by FITC-labeled goat anti-rabbit IgG, and then evaluated by FACS analysis showed that IgG from the post-immune serum had significantly higher binding to a broad spectrum of gram-negative bacteria (see Table 5) than the IgG prepared from the pre-immune serum. For bacteria culture conditions in these examples, see Bhattacharjee et al., *J. Infect. Dis.*, (1994), the contents of which are incorporated by reference.

In the absence of treatment with antibiotic (Imipenem) to expose the endotoxin core, the J5 specific IgG showed enhanced binding to at least 5 of the bacteria. With antibiotic treatment, there was enhanced binding of J5 specific IgG to all Gram-negative bacteria. There was no enhanced binding of the J5 specific IgG to the Gram-positive organism, *S. aureus*, which lacks endotoxin.

TABLE 5

Binding of Detoxified J5/Group B Meningococcal Outer Membrane Protein Vaccine-induced IgG to Imipenem-treated and Untreated Whole Bacteria

| Strain | Normal No Imipenem | Rabbit IgG Imipenem | J5-specific No Imipenem | Rabbit IgG Imipenem |
|---|---|---|---|---|
| E. coli 35 | 0.38 | 37.6 | 11.5 | 40.6 |
| S. aureus | 10.6 | 6.7 | 6.8 | 1.4 |
| E. coli 2961 | 22.3 | 20.1 | 35.9 | 57.8 |
| PA 2967 | 0.4 | 3.4 | 1.0 | 35.0 |
| E. cloacae | 0.4 | 2.2 | 0.9 | 55.0 |
| 2960 | 0.7 | 0.0 | 2.4 | 18.4 |
| 3037 | 0.4 | 0.0 | 1.1 | 22.9 |
| PA 2094 | 30.0 | 24.0 | 78.9 | 68.9 |
| EC2186 | 19.4 | 16.1 | 22.3 | 52.3 |
| E. aerogenes | 5.7 | 3.4 | 11.8 | 41.7 |
| E. cloacae 2203 | 52.1 | 55.0 | 49.0 | 86.7 |
| KP 2085 | 23.3 | 37.4 | 65.9 | 95.3 |

Data are expressed as percent population positive by FCAS. Positive gate defined by line drawn defining <5% non-specific binding (i.e., addition of secondary antibody, FITC-anti-rabbit IgG, to bacteria in absence of anti-rabbit IgG).

Bacteria grown, washed, treated with imipenem or buffer, washed, incubated with normal or J5 vaccine-induced rabbit IgG, followed by FITC-labelled goat or anti-rabbit IgG. At least 5,000 bacterial particles evaluated.

EXAMPLE 11

Protection of Rats in the Neutropenic Rat Model of Sepsis

The neutropenic rat model has been described before. See Collins et al., *J. Infect. Dis.* 159: 1073 (1989); Opal et al., *J. Infect. Dis.* 161: 1148 (1990). Briefly, female Sprague-Dawley rats (125–175 g) were obtained from Charles River Breeding Laboratories (Wilmington, Mass.) Cefamandole was given intramuscularly at a dose of 100 mg/kg beginning 96 hours before bacterial challenge. Cyclophosphamide was given intraperitoneally at a dose of 150 mg/kg at time 0 and at a dose of 50 mg/kg at 72 hours. At times 0, 48 and 96 hours the challenge strain of *P. aeruginosa* was given orally via an orogastric tube. Animals were monitored for fever with a Horiba non-contact digital infrared thermometer (Markson Science, Phoenix) and received antiserum or IgG fractions derived from the antiserum, at 9.0 ml/kg, intravenously via tail vein at the onset of fever (temperature >38.0° C., which was usually day 5 or 6). Control animals received normal saline on the same schedule. The animals were observed for 12 days and deaths were recorded. In a preliminary experiment, purified IgG was given at 3.0 ml/kg, 6.0 ml/kg and 9.0 ml/kg respectively (Total IgG=1.6 mg/ml) to three groups of rats. Blood samples were collected from the rats at 1, 6 and 24 hours post infusion and were analyzed by ELISA for anti-J5 LPS titers. The rat sera were also analyzed for endotoxin content. In this model neutrophils typically begin to return on days 9 to 10, and this is monitored by blood smear analysis on approximately 10% of animals during each experiment.

IgG was isolated from the post-immune serum of rabbit #62 which had been immunized with J5 LPS-NMGBOMP non-covalent complex vaccine. This IgG gave significant protection against challenge with lethal doses of a virulent strain of *P. aeruginosa* 12:4:4. Six out of 10 rats (60%) were protected compared to none of 10 rats treated with the control pre-immune serum IgG (p<0.02) see FIG. 1.

IgG was also prepared from the preimmune serum of rabbit #42374 which had been immunized with the J5 DLPS-NMGBOMP complex vaccine. Five of ten rats were protected by passive transfer of this IgG compared to none of ten rats treated with the preimmune serum IgG (P<0.02); see FIG. 1.

The invention claimed is:

1. A vaccine comprising a non-covalent complex of a purified, detoxified lipopolysaccharide endotoxin of *Escherichia coli* strain J5 and a purified outer membrane protein of *Neisseria meningitidis*, wherein said vaccine is effective in immunizing a subject against infection by heterologous Gram negative bacteria by inducing IgG specific to *Escherichia coli* J5 LPS wherein said IgG binds to, or is cross-reactive with heterologous Gram negative bacteria.

2. The vaccine of claim 1, wherein said *Escherichia coli* strain J5 is of the Rc chemotype.

3. The vaccine of claim 1, wherein said *Neisseria meningitidis* is group B *Neisseria meningitidis*.

4. The vaccine of claim 1, wherein the weight ratio of said purified outer membrane protein to said purified detoxified endotoxin in said non-covalent complex is between 1 and 2.

5. The vaccine of claim 1, 2 or 3 comprising sterile 0.9% sodium chloride or QS21 adjuvant.

6. A method of actively immunizing a subject against infection by heterologous Gram negative bacteria comprising administering to said subject an immunizing dose of the vaccine of claim 1.

7. The method of claim 6, wherein said *Escherichia coli* strain J5 is of the Rc chemotype.

8. The method of claim 6, wherein said *Neisseria meningitidis* is group B *Neisseria meningitidis*.

* * * * *